United States Patent [19]

Cuscurida et al.

[11] Patent Number: 5,405,977
[45] Date of Patent: Apr. 11, 1995

[54] PROCESS FOR REMOVING ORGANIC HALIDES FROM ALKYLENE CARBONATES

[75] Inventors: Michael Cuscurida; Edward T. Marquis, both of Austin, Tex.

[73] Assignee: Huntsman Corporation, Salt Lake City, Utah

[21] Appl. No.: 45

[22] Filed: Jan. 4, 1993

[51] Int. Cl.⁶ .................................... C07B 301/32
[52] U.S. Cl. .................................... 549/541; 549/542
[58] Field of Search ........................... 549/541, 542

[56] References Cited

U.S. PATENT DOCUMENTS

| | | | |
|---|---|---|---|
| 2,773,070 | 12/1956 | Lichtenwalter et al. | 260/340.2 |
| 2,873,282 | 2/1959 | McClellan | 260/340.2 |
| 4,547,620 | 10/1985 | Miyata et al. | 565/852 |
| 4,786,741 | 11/1988 | Sachs | 549/730 |
| 4,962,237 | 10/1990 | Laycock | 568/618 |
| 4,962,281 | 10/1990 | Laycock | 528/413 |

FOREIGN PATENT DOCUMENTS 0297647  6/1988  European Pat. Off. .
63-181765  7/1988  Japan .

OTHER PUBLICATIONS

*Chemical Abstract* vol 114 (5) No. 41, 753g, Suzuki et al, 1990, "Catalysis by Synthetic Hydrotaluite–like Material in Halide Recharge Between, Alkylhalide".

W. J. Peppel, "Preparation and Properties of the Alkylene Carbonates", *Industrial and Engineering Chemistry*, vol. 50, No. 5, pp. 767–770 (May 1958).

Technical Bulletin by KW–2000 Group, Kyowa Chemical Company, Aug. 20, 1988.

*Primary Examiner*—C. Warren Ivy
*Assistant Examiner*—Raymond Covington
*Attorney, Agent, or Firm*—Russell R. Stolle

[57] ABSTRACT

A method for removing organic halide contaminants from alkylene carbonates is disclosed. Organic halide contaminants are removed from alkylene carbonates by contacting the contaminated alkylene carbonate with hydrotalcite.

7 Claims, No Drawings

PROCESS FOR REMOVING ORGANIC HALIDES FROM ALKYLENE CARBONATES

BACKGROUND OF THE INVENTION

1. Field of the Invention

The invention relates to the purification of alkylene carbonates, also known as glycol carbonates, and more particularly to the removal of organic halide compounds from alkylene carbonates.

2. Description of Related Methods

The reaction, of alkylene oxides with carbon dioxide in the presence of a catalyst is the conventional route to the preparation of alkylene carbonates. U.S. Pat. No. 2,773,070 to Lichtenwalter et al. discloses a process for preparing alkylene carbonates using an ammonium halide catalyst. U.S. Pat. No. 2,873,282 to Mc Clellan discloses the use of certain quaternary ammonium compounds to catalyze the reaction of alkylene oxides and carbon dioxide. W. J. Peppel, in "Preparation and Properties of the Alkylene Carbonates," *Industrial and Engineering Chemistry*, vol. 50, no. 5, pp. 767-770 (May 1958), provides an overview of the various methods then known for the preparation of alkylene carbonates.

It appears that most of the known processes employ halogen-based catalysts. For example, U.S. Pat. No. 4,786,741 to Sachs teaches a process for preparing alkylene carbonates that employs a catalyst selected from the group consisting of organic quaternary ammonium halides, organic quaternary phosphonium halides, organic sulfonium halides, and organic antimony halides. European Patent Application 0 297 647 claims a process wherein alkylene carbonates are prepared using a catalyst comprising an alkali or alkaline earth metal halide. Japanese Patent Application Number 63-181765 also discloses a method for the preparation of alkylene carbonates using an alkali halide catalyst. Typical halogen-containing catalysts are Friedel-Crafts catalysts, such as $AlCl_3$, $FeCl_3$, $SnCl_4$, $BF_3$ and other Lewis acids, and Ziegler catalysts, such as combinations containing a transition-metal halogen compound and a metal hydride or metal alkyl.

Halide-based catalysts, however, tend to contaminate the alkylene carbonate product with halogen compounds. These halogen contaminants are present both as ionic halides (residual catalyst) and as organic halide compounds. In the case of volatile alkylene carbonates, careful distillation removes the carbonates overhead while leaving ionic halides in the distillation bottoms. In processes where the product may be contaminated with ionic halides, it is known to remove ionic halides in the form of residual catalyst by contacting the contaminated product with one of a variety of adsorbents. For example, U.S. Pat. No. 4,547,620 to Miyata et al. discloses the use of a hydrotalcite to remove ionic halides in the form of residual catalyst from contaminated products.

Organic halides, however, generally are much more difficult to remove. In an organic halide, the halide is covalently bonded rather than being the free ionic species that it is in an ionic halide. Additionally, organic halide contaminants, such as $BrCH_2CH_2OH$, $BrCH_2CH_2OCH_2CH_2OH$, $BrCH_2CH_2OCH_2CH_3$, $BrCH_2CH_2OCH_2CH_2OCH_2CH_3$, and $BrCH_2CH_2OCH_2CH_2Br$, that are formed, for example, when ethylene carbonate is prepared using a tetraalkyl ammonium bromide catalyst, have a boiling point close enough to the boiling point of ethylene carbonate to make separation by distillation very difficult. Applicants, however, have discovered that alkylene carbonates that are contaminated with organic halide compounds may be purified by contacting the contaminated alkylene carbonates with hydrotalcite. Until the discovery disclosed in the present application, it was unknown that organic halide compounds could be removed from contaminated products using hydrotalcite.

SUMMARY OF THE INVENTION

The invention concerns a process for removing organic halide compounds from alkylene carbonates, comprising contacting a mixture containing alkylene carbonate and one or more organic halide compounds with a hydrotalcite compound represented by the following formula:

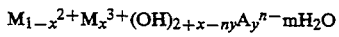

$$M_{1-x}^{2+}M_x^{3+}(OH)_{2+x-ny}A_y^{n-}\cdot mH_2O$$

wherein $M^{2+}$ represents a divalent metal ion selected from the group consisting of $Mg^{2+}$, $Zn^{2+}$, $Ca^{2+}$, $Ni^{2+}$, $Co^{2+}$, $Mn^{2+}$, and $Cu^{2+}$, and $M^{3+}$ represents a trivalent metal ion selected from the group consisting of $Al^{3+}$, $Fe^{3+}$, and $Cr^{3+}$, and $A^{n-}$ represents an anion having a valence of n selected from the group consisting of $HCO_3^-$, $OH^-$, and $CO_3^{2-}$, and x, y, and m are each a positive number and satisfy the following conditions: $0.1<x<0.5$, $0.1<y<0.4$, and $0 \leq m \leq 1$, under non-aqueous conditions, and separating the treated alkylene carbonate from the hydrotalcite compound.

The invention also concerns a process for removing organic halide compounds from alkylene carbonates, comprising contacting a mixture containing alkylene carbonate and one or more organic halide compounds with a hydrotalcite compound represented by the following formula: $Mg_{1-x}Al_xO_{1+x/2}$, wherein $x=0.25$ to $0.3$, under non-aqueous conditions and at a temperature at which the organic halide compound is not liberated from the hydrotalcite compound, and separating the alkylene carbonate from the hydrotalcite compound.

DESCRIPTION OF THE PREFERRED EMBODIMENTS

Alkylene carbonates are prepared by the reaction of alkylene oxides with carbon dioxide in the presence of a catalyst. Alkylene oxides that may be employed in the reaction include those of the oxirane system. Preferably the alkylene oxide has the following structural formula:

in which R and $R^1$ may be selected from the group consisting of hydrogen, aryl groups having from 6 to about 20 carbon atoms, alkyl groups containing from 1 to about 20 carbon atoms, cycloalkyl groups containing from 5 to about 20 carbon atoms, and alkenyl groups containing from 2 to about 20 carbon atoms. Preferably, R is hydrogen and $R^1$ is selected from the group consisting of hydrogen, aryl groups having from 6 to about 12 carbon atoms, alkyl groups containing from 1 to about 5 carbon atoms, cycloalkyl groups containing from 5 to about 12 carbon atoms, and alkenyl groups containing from 2 to about 5 carbon atoms. More preferably, R is hydrogen and $R^1$ is selected from the group consisting of hydrogen, alkyl groups containing from 1 to about 5 carbon atoms, and alkenyl groups containing from 2 to about 5 carbon atoms. Especially preferred are ethylene oxide and propylene oxide. The oxirane compounds, as shown by the formula above, have the ring oxygen atom attached to two adjacent carbon atoms.

The reaction may be carried out at a temperature of from about 100° to about 225° C. or higher, preferably from about 175° to about 215° C. The reaction may be carried out at atmospheric pressure or, preferably, under a pressure of about 300 psig or greater. More preferably, the reaction is carried out under a pressure of about 1000 to about 3000 psig. The reaction may be conducted either batch-wise or continuously.

In a continuous reaction, alkylene oxide and carbon dioxide are introduced to a continuous reactor containing the catalyst, from which a portion of the reaction mixture may be continuously recirculated through the reactor. Another portion of this reaction mixture is continuously withdrawn and flashed to remove unreacted carbon dioxide and alkylene oxide, which are compressed and returned to the reactor. The residue from the flashing treatment is subjected to distillation to separate the alkylene carbonate from the catalyst solution. Residual catalyst solution or slurry (bottoms) may be returned directly to the reactor. At times, it may be desirable to discard a portion of the recovered catalyst stream to prevent accumulation of unwanted by-products in the catalyst stream.

Alternatively, batches of alkylene oxide and catalyst may be introduced into an autoclave or kettle type reactor. The desired pressure may be built up by introducing carbon dioxide. Typically, the reaction mixture is heated to reaction temperature, agitated, and held under a superatmospheric pressure of carbon dioxide.

The alkylene oxide and carbon dioxide should be mixed in proportion to provide an excess of carbon dioxide over and above the stoichiometric amount required for reaction. This excess may be on the order of from about 1.1 moles of carbon dioxide per mole of alkylene oxide to about 10 moles of carbon dioxide per mole of alkylene oxide. An excess of alkylene oxide should be avoided, because it results in undesired by-products, chiefly alkylene oxide polymers, and because explosive conditions may result.

Catalysts useful in the preparation of alkylene carbonates include halogen-containing catalysts. Typical halogen-containing catalysts are Friedel-Crafts catalysts, such as $AlCl_3$, $FeCl_3$, $SnCl_4$, $BF_3$ and other Lewis acids, and Ziegler catalysts, such as combinations containing a transition-methyl halogen compound and a metal hydride or metal alkyl. Applicants have found tetraalkyl ammonium halides to be very effective catalysts. See, for example, U.S. Pat. No. 2,773,070, incorporated herein by reference. The preferred catalyst is a bromide catalyst, particularly tetraethyl ammonium bromide. The amount of catalyst used should be from about 0.1% to about 10%, preferably from about 1% to about 5%, based on the weight of the reaction mixture. In general, the greater the catalyst concentration, within these limits, the more rapid and complete the reaction. Catalyst may be separated from the alkylene carbonate product by wiped film evaporator distillation.

As discussed above, halogen-containing catalysts will form organic halide by-products during the reaction of the alkylene oxide and carbon dioxide. These undesirable organic halide by-products are of the group consisting of halo-alkanols, halo-ethers, and halo-etheralkanols derived by reaction of the halide with alkylene oxide, and by further subsequent reaction of some of the initial by-products with additional alkylene oxide. Prior to Applicants' discovery, it was thought that these organic halides were very difficult to remove. In an organic halide, the halide is covalently bonded rather than being the free ionic species that it is in an ionic halide. These organic halide by-products are non-ionic compounds. Additionally, organic halide contaminants, such as $BrCH_2CH_2OH$ (bromoethanol), $BrCH_2CH_2OCH_2CH_2OH$ (2-bromoethoxy ethanol), $BrCH_2CH_2OCH_2CH_3$ (2-bromoethyl ether), $BrCH_2CH_2OCH_2CH_2OCH_2CH_3$ (1-(2-bromoethoxy)-2-ethoxy ethane, and $BrCH_2CH_2OCH_2CH_2Br$ (bis(2-bromoethyl) ether), that are formed, for example, when ethylene carbonate is prepared using a bromide catalyst, have a boiling point close enough to the boiling point of ethylene carbonate to make separation by distillation very difficult. In the case of propylene carbonate preparation, structures similar to those listed above are formed, except that isomers of the bromopropanols, bromo ethoxy propanes, bis bromo propyl ethers, etc. are formed. Catalysts containing other halides form homologous compounds. Thus, the Br in the above structures may be replaced with F, Cl, or another halogen. Applicants, however, have discovered that alkylene carbonates that are contaminated with organic halide compounds may be purified by contacting the contaminated alkylene carbonates with hydrotalcite.

According to the present invention, organic halides are removed from alkylene carbonates by contacting a mixture containing alkylene carbonate and one or more organic halide compounds with a hydrotalcite compound represented by the following formula:

$$M_{1-x}^{2+}M_x^{3+}(OH)_{2+x-ny}A_y^{n-}mH_2 \qquad (I)$$

wherein $M^{2+}$ represents a divalent metal ion selected from the group consisting of $Mg^{2+}$, $Zn^{2+}$, $Ca^{2+}$, $Ni^{2+}$, $Co^{2+}$, $Mn^{2+}$, and $Cu^{2+}$, and $M^{3+}$ represents a trivalent metal ion selected from the group consisting of $Al^{3+}$, $Fe^{3+}$, and $Cr^{3+}$, and $A^{n-}$ represents an anion having a valence of n selected from the group consisting of $HCO_3^-$, $OH^-$, and $CO_3^{2-}$, and x, y, and m are each a positive number and satisfy the following conditions: $0.1 < x < 0.5$, $0.1 < y < 0.4$, and $0 \leq m \leq 1$, and separating the treated alkylene carbonate from the hydrotalcite compound.

In formula (I), above, a divalent metal ion selected from $Mg^{2+}$, $Zn^{2+}$, $Ca^{2+}$, and $Ni^{2+}$ is preferred as $M^{2+}$, and a divalent metal ion selected from $Mg^{2+}$ and $Zn^{2+}$ is more preferred. Preferably, $M^{3+}$ is a trivalent metal ion selected from $Al^{3+}$ and $Fe^{3+}$, and more preferably $Al^{3+}$. Preferably, $A^{n-}$ is an anion having a valence of n selected from the group consisting of $OH^-$ and $CO_3^{2-}$. It is especially preferred that the hydrotalcite used in the present inventive process have the formula $Mg_{1-x}Al_xO_{1+x/2}$, wherein $x = 0.25$ to $0.3$. Examples of commercially available hydrotalcites having a structure in accordance with the latter formula are KW-2000, KW-2100, KW-2200, and KW-2300, each commercially available from Kyowa Chemical Industry Co., Ltd., of Japan. Most preferred is KW-2000, for which $x = 0.3$, and which has an average particle size of $70.0\mu$, a specific surface area (BET method) of 172 $m^2/g$, an 1 g-loss of 3.8%, and an apparent bulk density of 44 ml/10 g.

The hydrotalcites used in the present invention also may be prepared, for example, in accordance with the process disclosed in Japanese Patent Publication No. 3353/1977. For example, such hydrotalcites may be prepared by reacting (a) a compound of a divalent cation $M^{2+}$ selected from the group consisting of $Mg^{2+}$, $Zn^{2+}$, $Ca^{2+}$, $Ni^{2+}$, $Co^{2+}$, $Mn^{2+}$, and $Cu^{2+}$, and (b) a compound of a trivalent cation $M^{3+}$ selected from the group consisting of $Al^{3+}$, $Fe^{3+}$, and $Cr^{3+}$, and (c) a compound of an anion $A^{n-}$ (n=1-2) selected from the group consisting of $HCO_3^-$, $OH^-$, and $CO_3^{2-}$, and (d) a substance capable of yielding $OH^-$, in a liquid medium, preferably in an aqueous medium, so that the relations $0.1<x<0.5$ and $0.1<y<0.4$ are satisfied. This process is more fully described in U.S. Pat. No. 4,547,620, incorporated herein by reference.

The hydrotalcite may be contacted with the contaminated alkylene carbonate at a temperature of from about $-20°$ C. to about $300°$ C., preferably at least at room temperature. It is more preferred that the hydrotalcite is contacted with the contaminated alkylene carbonate at elevated temperature, but not at a temperature so high as to cause organic halide compounds adsorbed by the hydrotalcite to be liberated from the hydrotalcite. The pressure may be from about atmospheric to about 1000 psig. The contaminated alkylene carbonate may be treated with the hydrotalcite batch-wise in a stirred slurry, or continuously using a fixed bed of hydrotalcite, such as by filling a column with hydrotalcite and passing the contaminated alkylene carbonate through the packed column. The contaminated alkylene carbonate should be contacted with the hydrotalcite under non-aqueous conditions. As used herein, the term non-aqueous shall mean a system that does not contain a substantial amount of water, and does not exclude systems that contain a small amount of water.

Preferably, the hydrotalcite used will have good sedimentability and filterability, and may be separated from the alkylene carbonate easily, such as by filtration. The hydrotalcite may be regenerated after use, according to the procedure disclosed in U.S. Pat. No. 4,547,620.

The invention will be further illustrated by the following examples, which are given by way of illustration and not as limitations on the scope of this invention. The entire text of every patent, patent application or other reference mentioned above is hereby incorporated herein by reference.

In the examples detailed in the table below, the alkylene carbonate products were separated by distillation from the tetraalkyl ammonium bromide catalysts. In each example below, approximately 150.0 g of alkylene carbonate was stirred with approximately 15.0 g of Hydrotalcite KW-2000 from Kyowa Chemical Industry Co., Ltd. The mixtures were stirred for the times and at the temperatures noted in Table I, below. The Comparative Examples of Table II were performed in a similar manner, using other adsorbents.

TABLE 1

EXAMPLES

| Ex. No. | Material Treated, Treatment Conditions | Pt—Co Color | pH | % $H_2O$ | ppm Br | ppm N | GLC % PG or EG | GLC % PG or EC | ppm Mg | ppm Al |
|---|---|---|---|---|---|---|---|---|---|---|
| 1 | PC Starting Material | 30 | 6.68 | 0.020 | 170 | 15 | 0.041 | 99.950 | — | — |
| A. | 10% KW-2000, R.T., 6.0 hrs. | NES | 7.20 | 0.110 | 81 | 9 | 0.079 | 99.412 | 1.5 | <1 |
| B. | 10% KW-2000, 60° C., 5.0 hrs. | NES | 7.27 | 0.030 | 26 | 13 | 0.798 | 99.080 | 23 | 13 |
| 2. | EC-50, starting material | 10 | 6.79 | 0.008 | 469 | 52 | | | — | — |
| A. | 10% KW-2000, R.T. 6.0 hrs. | NES | 6.84 | 0.220 | 232 | 39 | | | 3.6 | <1 |
| B. | 10% KW-2000, 60° C., 5.0 hrs. | NES | 6.73 | 0.060 | 284 | 53 | | | 2.5 | <1 |
| 3. | PC, starting material | 15 | 6.85 | 0.010 | 135 | 8 | 0.065 | 99.132 | — | — |
| A. | 10% KW-2000, R.T., 6.0 hrs. | 10 | 6.74 | 0.120 | 104 | 5 | 0.097 | 99.614 | 4.1 | 1.9 |
| B. | 10% KW-2000, 60° C., 5.0 hrs. | 5 | 6.88 | NES | 36 | 7 | 0.896 | 98.991 | 2.6 | 10 |
| 4. | PC, starting material | 5 | 6.88 | 0.010 | 111 | 5 | 0.000 | 99.990 | — | — |
| A. | 10% KW-2000, R.T., 6.0 hrs. | 5 | 6.66 | 0.120 | 20 | 2 | 0.082 | 99.727 | 5.1 | 2.2 |
| B. | 10% KW-2000, 60° C., 5.0 hrs. | 5 | 7.12 | 0.070 | 11 | 3 | 0.878 | 99.046 | 0.6 | <1 |
| 5. | PC, starting material | 5 | 6.61 | 0.008 | 90 | 8 | 0.000 | 99.992 | — | — |
| A. | 10% KW-2000, R.T., 6.0 hrs. | 5 | 6.72 | 0.140 | 12 | 3 | 0.079 | 99.731 | 4.1 | 1.9 |
| B. | 10% KW-2000, 60° C., 5.0 hrs. | 5 | 6.99 | 0.060 | 17 | 6 | 0.890 | 99.044 | 0.6 | <1 |
| 6. | PC, starting material | 10 | 6.51 | 0.008 | 54 | 4.5 | 0.000 | 99.991 | — | — |
| A. | 10% KW-2000, R.T., 6.0 hrs. | 10 | 6.77 | 0.130 | 11 | 2 | 0.084 | 99.761 | 9.1 | 3.6 |
| B. | 10% KW-2000, 60° C., 5.0 hrs. | 5 | 6.95 | 0.050 | 20 | 4 | 0.858 | 99.079 | 2.7 | <1 |
| 7. | PC, starting material | 5 | 6.81 | 0.009 | 22 | 6 | 0.000 | 99.964 | — | — |
| A. | 10% KW-2000, R.T., 6.0 hrs. | 10 | 6.74 | 0.120 | 16 | 3 | 0.085 | 99.738 | 6.5 | 2.4 |
| B. | 10% KW-2000, 60° C., 5.0 hrs. | 5 | 7.06 | 0.080 | 21 | 5 | 0.724 | 99.154 | 1.5 | <1 |
| 8. | PC, starting material | 5 | 6.35 | 0.009 | 13 | 4 | 0.000 | 99.991 | — | — |
| A. | 10% KW-2000, R.T., 6.0 hrs. | 10 | 6.80 | 0.150 | 13 | 3 | 0.135 | 99.677 | 3.8 | 1.7 |
| B. | 10% KW-2000, 60° C., 5.0 hrs. | 5 | 6.99 | 0.060 | 9 | 3 | 0.823 | 99.104 | 0.4 | <1 |

PC = propylene carbonate;
R.T. = room temperature;
NES = not enough sample;
GLC = gas liquid chromatography;
Pt = platinum;
Co = cobalt.

COMPARATIVE EXAMPLES

| Ex. No. | Material Treated, Treatment Conditions | Pt—Co Color | pH | % $H_2O$ | ppm Br | ppm N | GLC % PG or EG | GLC % PC or EC |
|---|---|---|---|---|---|---|---|---|
| | PC, starting material | 15 | 6.85 | 0.010 | 135 | 8 | 0.065 | 99.132 |
| 1 | 10% magnesol, 60° C., 5.0 hrs | | | | 213 | 3 | 3.190 | 96.301 |
| 2 | 10% CaO, 60° C., 5.0 hrs | | | | 98 | 7 | 0.255 | 99.351 |
| 3 | 10% Ca(OH)$_2$, 60° C., 5.0 hrs | | | | 82 | 8 | 1.092 | 98.552 |
| 4 | 10% BaO, 60° C., 5.0 hrs | | | | 128 | 7 | 0.112 | 99.629 |

-continued

| | COMPARATIVE EXAMPLES | | | | | | | |
|---|---|---|---|---|---|---|---|---|
| Ex. No. | Material Treated, Treatment Conditions | Pt—Co Color | pH | % $H_2O$ | ppm Br | ppm N | GLC % PG or EG | GLC % PC or EC |
| 5 | 10% Ba(OH)$_2$, 60° C., 5.0 hrs | | | | 65 | 8 | 7.641 | 91.622 |
| 6 | 10% MgO, 60° C., 5.0 hrs | | | | 117 | 7 | 1.318 | 98.210 |
| 7 | 10% Basic Alumina, 60° C., 5.0 hrs | | | | 72 | 7 | 1.917 | 97.609 |
| | PC, starting material | .5 | 6.88 | 0.010 | 111 | 5 | 0.000 | 99.990 |
| 8 | 10% Magnesol, 60° C., 5.0 hrs | | | | 52 | 2 | 1.999 | 97.432 |
| 9 | 10% CaO, 60° C., 5.0 hrs | | | | 33 | 16 | 0.253 | 99.180 |
| 10 | 10% Ca(OH)$_2$, 60° C., 5.0 hrs | | | | 27 | 4 | 0.871 | 98.727 |
| 11 | 10% BaO, 60° C., 5.0 hrs | | | | 24 | 4 | 0.054 | 99.057 |
| 12 | 10% Ba(OH)$_2$, 60° C., 5.0 hrs | | | | 38 | 4 | 8.119 | 90.891 |
| 13 | 10% MgO, 60° C., 5.0 hrs | | | | 32 | 3 | 1.308 | 98.218 |
| 14 | 10% Basic Alumina, 60° C., 5.0 hrs | | | | 24 | 3 | 1.961 | 97.759 |

We claim:

1. A process for removing organic halide compounds from alkylene carbonates, comprising contacting a mixture containing alkylene carbonate and one or more organic halide compounds with a hydrotalcite compound represented by the following formula:

$$M_{1-x}^{2+}M_x^{3+}(OH)_{2+x-ny}A_y^{n-} \cdot mH_2O$$

wherein $M^{2+}$ represents a divalent metal ion selected from the group consisting of $Mg^{2+}$, $Zn^{2+}$, $Ca^{2+}$, $Ni^{2+}$, $Co^{2+}$, $Mn^{2+}$, and $Cu^{2+}$, and $M^{3+}$ represents a trivalent metal ion selected from the group consisting of $Al^{3+}$, $Fe^{3+}$, and $Cr^{3+}$, and $A^{n-}$ represents an anion having a valence of n selected from the group consisting of $HCO_3^-$, $OH^-$, and $CO_3^{2-}$, and x, y, and m are each a positive number and satisfy the following conditions: $0.1 < x < 0.5$, $0.1 < y < 0.4$, and $0 \leq m \leq 1$, under non-aqueous conditions, wherein an organic halide compound is adsorbed onto the surface of said hydrotalcite compound, and separating the treated alkylene carbonate from the hydrotalcite compound.

2. The process of claim 1, wherein the organic halide compound is selected from the group consisting of halo-alkanols, halo-ethers, and halo-etheralkanols.

3. The process of claim 1, wherein the organic halide compound is selected from the group consisting of $BrCH_2CH_2OH$, $BrCH_2CH_2OCH_2CH_2OH$, $BrCH_2CH_2OCH_2CH_3$, $BrCH_2CH_2OCH_2CH_2OCH_2CH_3$, and $BrCH_2CH_2OCH_2CH_2Br$.

4. A process for removing organic halide compounds from alkylene carbonates, comprising contacting a mixture containing alkylene carbonate and one or more organic halide compounds with a hydrotalcite compound represented by the following formula: $Mg_{1-x}Al_xO_{1+x/2}$, wherein $x = 0.25$ to 0.3, under non-aqueous conditions and at a temperature at which the organic halide compound is not liberated from the hydrotalcite compound onto the surface of which the organic halide compound has been adsorbed, and separating the alkylene carbonate from the hydrotalcite compound.

5. The process of claim 4, wherein the organic halide compound is selected from the group consisting of halo-alkanols, halo-ethers, and halo-etheralkanols.

6. The process of claim 4, wherein the organic halide compound is selected from the group consisting of $BrCH_2CH_2OH$, $BrCH_2CH_2OCH_2CH_2OH$, $BrCH_2CH_2OCH_2CH_3$, $BrCH_2CH_2OCH_2CH_2OCH_2CH_3$, and $BrCH_2CH_2OCH_2CH_2Br$.

7. A process for removing organic halide compounds from alkylene carbonates, comprising contacting a mixture containing alkylene carbonate and one or more organic halide compounds selected from the group consisting of halo-alkanols, halo-ethers, and halo-etheralkanols, with a hydrotalcite compound represented by the following formula: $Mg_{1-x}Al_xO_{1+x/2}$, wherein $x = 0.25$ to 0.3, under non-aqueous conditions and at a temperature at which the organic halide compound is not liberated from the hydrotalcite compound onto the surface of which the organic halide compound has been adsorbed, and separating the alkylene carbonate from the hydrotalcite compound.

* * * * *